Nov. 24, 1964 W. E. SILVA Plant Pat. 2,454
BLACK LOCUST TREE
Filed June 27, 1963
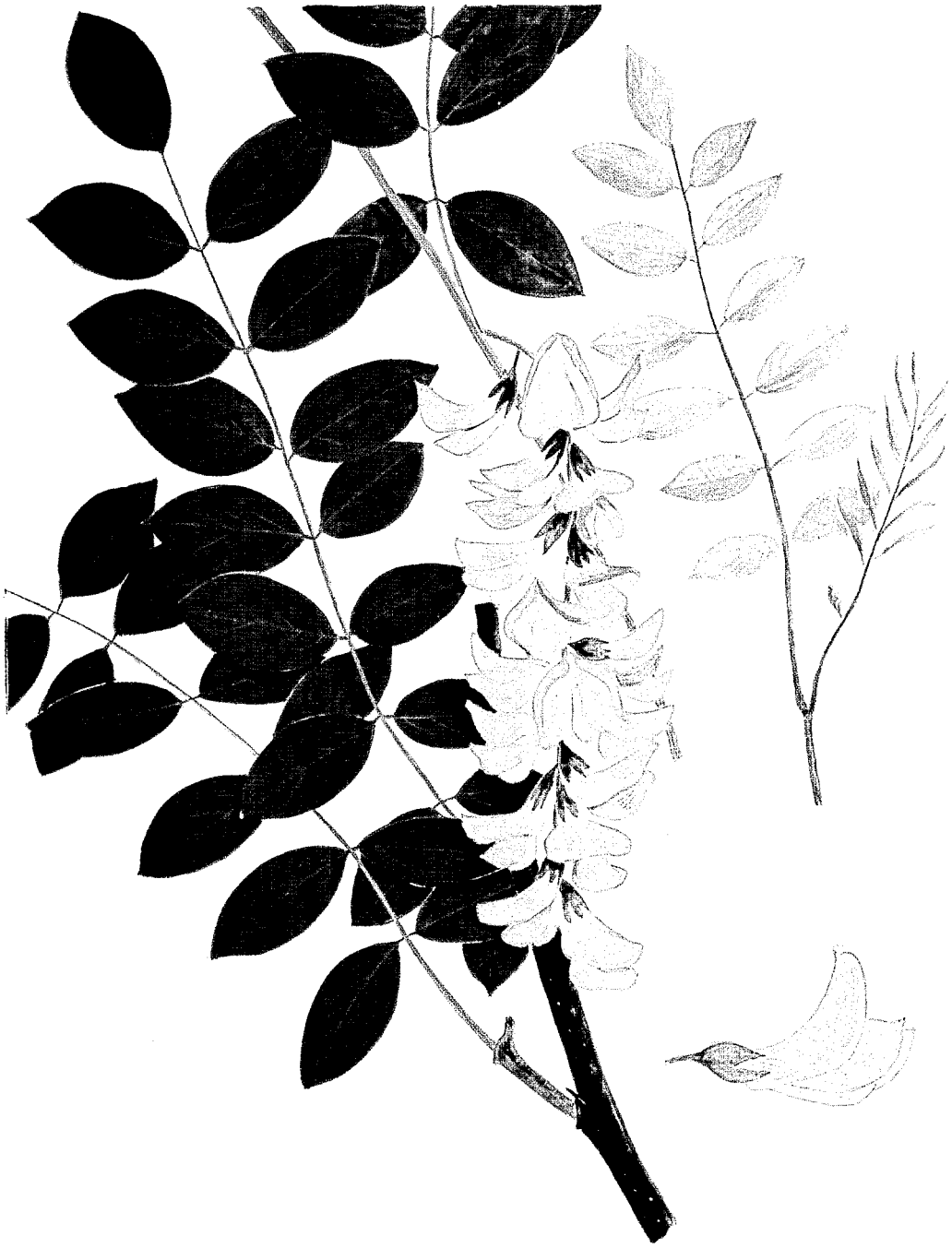
WITNESS
Samuel H. Groom
INVENTOR
WILLIAM E. SILVA
Rummler & Snow
ATTYS.

United States Patent Office

Plant Pat. 2,454
Patented Nov. 24, 1964

2,454
BLACK LOCUST TREE
William E. Silva, 408 Watertrough Road,
Sebastopol, Calif.
Filed June 27, 1963, Ser. No. 291,608
1 Claim. (Cl. Plt.—51)

My present disclosure concerns a new and distinct variety of black locust tree developed by me in the course of breeding efforts carried on at my nursery at Sebastopol, California, since 1949, in an effort to produce a black locust tree having better foliage and flower characteristics and a better appearance as a tree than the heretofore known and available varieties.

My new variety of black locust tree originated as a selected seedling developed by a cross between *Robinia pseudoacacia decaisneana* (unpatented), as the seed parent, and *Robinia pseudoacacia* "Monument" (unpatented), as the pollen parent. This new variety was noted to have a very distinctive purple coloring of its blooms, which gives the tree a very attractive and unusual appearance during the blooming season, and to have improved growth habits over its parents. Accordingly the new variety was selected for propagation and asexual reproduction of the plant has been carried on by me and under my supervision, in my nursery at Sebastopol, California, by cuttings, budding and grafting, with the result that the novel characteristics of the new variety have been found to be fixed and to hold true.

The distinctive blooms and foliage of my new variety of black locust tree are shown in the accompanying full color drawings wherein the large central figure shows a single raceme, or blossom cluster, together with a portion of a branch and mature foliage; the upper right hand figure is a detail showing the color and form of new growth appearing at the top of the tree; and the lower right hand figure is an enlarged view of a single flower, shown at substantially twice the scale of the other views, illustrating its distinctive coloring.

The following is a detailed description of my new variety of black locust tree, the color designations being according to "A Dictionary of Color" by Maerz and Paul and in the order of Plate-Column-Line.

*The Plant*

Origin: Seedling.
Parentage:
- *Seed parent.*—*Robinia pseudoacacia decaisneana* (unpatented).
- *Pollen parent.*—*Robinia pseudoacacia* "Monument" (unpatented).

Classification: Hybrid Robinia.
Form: Tree.
Height: 40 to 50 feet in 8 years.
Growth: Fast, sturdy and upright, with strong upright branches.
Foliage:
- *Quantity.*—Abundant.
- *Size of mature leaf.*—8 to 14 inches long.
- *Type of leaf.*—Odd-pinnate, with a single terminal leaflet and two opposing rows of 6 to 8 leaflets on a sturdy rachis.
- *Size of leaflet.*—1⅜ inches wide x 2½ inches long. Shape—elliptic.
- *Texture of leaflets.*—Smooth and glossy.
- *Color, mature leaf.*—22L4 to 22L6.
- *Petioles.*—Length approximately one-third inch.
- *Ribs and veins.*—Very light in size.

- *Rachis.*—Color—25L5 to 25L6 with a red tone 6J6 on the upper surface.

Basic color of old bark is 56L4 to 56L6.
Plant has small spines and prickles of brown color and about one-fifth inch long.
New growth, at top of tree during spring and summer, appears with small leaflet sprouts of light green color 21L1 to 21L2 overlaid with a bronze-like tone of 13L5 to 13L7. These age to approximately half-size leaflets having a few streaks of bronze 13L7 on one side of the mid-rib and a substantially complete overlay of the bronze 13L7 on the opposite side of the mid-rib.

*The Flowers*

Blooms: Profusely, once in the spring (April and May in California) and, if irrigated, the plant has a tendency to produce a few blooms in the fall.
Size: Very large racemes, 8 inches in length and at least two inches in diameter.
Borne: Usually singly—but sometimes in clusters of two racemes—pendulous.
Florets:
- *Form.*—Papilionaceous—opens slowly.
- *Size.*—⅞ inch long x 1 inch wide.
- *Texture.*—Heavy, leathery.
- *Color of Petals.*—Purple—51K6 to 51J6 and having whitish area at base of petals.
- *Calyx.*—Long, legume funnel, and of smooth glandular aspect. Color—6J6 with over color of 14J2 at base and on stem.
- *Peduncle.*—Length—8 inches. Color—green—22L5. Sturdy and drooping.

Quality: Blooms are fragrant and last about two weeks on the plant. The blooms are not affected by wet or hot weather.
Genital organs:
- *Stamens.*—Anthers—9 in number—½ inch long. Filaments—1/12 inch long—white in color.
- *Pollen.*—Small amount—yellow in color.
- *Pistils.*—1–3 inches long.
- *Stigmas.*—White in color.

*Fruit*

Pea pod shaped, no seeds.

My new variety of black locust tree most nearly resembles its parent *Robinia pseudoacacia decaisneana* and is particularly distinguished by the beautiful purple color of its pendulous racemes. The new variety is also distinguished by the reddish bronze coloring of the new growth foliage at the top of the tree, in the spring and summer; by the fact that the plant never bears seeds, has no bristles and has very small prickles; and the fact that the new plant will withstand excessive moisture better, and blossoms from two weeks to one month earlier than other varieties of black locust grown in the same locality.

Having now shown and described my new variety of black locust tree, I claim:

A new and distinct variety of black locust tree, substantially as shown and described, particularly characterized by its large blooms comprising pendulous racemes having florets of purple color; by its vigorous habit of growth and abundance of foliage; and by its habit of blooming earlier than other varieties of black locust grown in the same locality.

No references cited.

ABRAHAM G. STONE, *Primary Examiner.*